(12) United States Patent
Hastings, Jr. et al.

(10) Patent No.: US 7,824,375 B2
(45) Date of Patent: Nov. 2, 2010

(54) SLITTABLE DELIVERY DEVICE FOR THE DELIVERY OF A CARDIAC SURGICAL DEVICE

(75) Inventors: John Hastings, Jr., Minneapolis, MN (US); Dale Price, Coon Rapids, MN (US); Heather Helgeson, Robert, WI (US); Brian Bechtold, Clearwater, MN (US)

(73) Assignee: Pacesetter, Inc., Sylmar, CA (US)

( * ) Notice: Subject to any disclaimer, the term of this patent is extended or adjusted under 35 U.S.C. 154(b) by 2 days.

(21) Appl. No.: 12/248,802

(22) Filed: Oct. 9, 2008

(65) Prior Publication Data

US 2010/0094225 A1    Apr. 15, 2010

(51) Int. Cl.
*A61M 5/178* (2006.01)
(52) U.S. Cl. .................... 604/160; 604/99.02
(58) Field of Classification Search ............. 604/160, 604/161, 163
See application file for complete search history.

(56) References Cited

U.S. PATENT DOCUMENTS

| | | | | |
|---|---|---|---|---|
| 4,354,491 A * | 10/1982 | Marbry | | 604/160 |
| 4,402,685 A * | 9/1983 | Buhler et al. | | 604/523 |
| 4,921,479 A * | 5/1990 | Grayzel | | 604/509 |
| 4,997,424 A | 3/1991 | Little | | |
| 5,188,605 A * | 2/1993 | Sleep | | 604/158 |
| 5,221,263 A * | 6/1993 | Sinko et al. | | 604/161 |
| 5,312,355 A * | 5/1994 | Lee | | 604/160 |
| 5,755,693 A * | 5/1998 | Walker et al. | | 604/160 |
| 6,083,207 A * | 7/2000 | Heck | | 604/256 |
| 6,159,198 A * | 12/2000 | Gardeski et al. | | 604/523 |
| 6,497,681 B1 | 12/2002 | Brenner | | |
| 6,712,791 B2 * | 3/2004 | Lui et al. | | 604/167.04 |
| 6,966,896 B2 | 11/2005 | Kurth et al. | | |
| 2003/0050604 A1 * | 3/2003 | Lui et al. | | 604/167.06 |
| 2004/0054330 A1 * | 3/2004 | Kurth et al. | | 604/160 |
| 2004/0267202 A1 * | 12/2004 | Potter | | 604/158 |
| 2006/0052749 A1 * | 3/2006 | Moyer | | 604/160 |

* cited by examiner

*Primary Examiner*—Nicholas D Lucchesi
*Assistant Examiner*—Gerald Landry, II

(57) ABSTRACT

Disclosed herein is a slittable delivery device for the delivery of a cardiac surgical device. The delivery device includes a hub and a shaft integrated into the hub. The shaft forms at least a segment of the circumferential surface of the hub. The delivery device may also include a hemostasis valve contained substantially within the hub and a cap on a proximal end of the hub. The cap may include an opening in the cap extending radially outward from a point near a radial center of the cap through a circumferential edge of the cap.

13 Claims, 12 Drawing Sheets

SLITTABLE DELIVERY DEVICE FOR THE DELIVERY OF A CARDIAC SURGICAL DEVICE

FIELD OF THE INVENTION

The present invention relates to medical apparatus and methods. More specifically, the present invention relates to delivery devices for implantable cardiac electrotherapy leads and other cardiac surgical devices and methods of manufacturing such delivery devices.

BACKGROUND OF THE INVENTION

Implantable pulse generators, such as pacemakers, defibrillators or implantable cardioverter defibrillators ("ICD") provide electrotherapy to cardiac tissue via implantable cardiac electrotherapy leads. Delivery devices, such as delivery catheters or sheaths, serve as a conduit for such leads and aid in the placement of the leads in specific cardiac anatomies during implantation of the pulse generator. Upon placement of the lead, the delivery catheter is removed and care is taken to not disrupt the position of the implanted lead. Non-disruptive removal is also advantageous when the delivery devices are used to deliver other cardiac surgical devices, such as inner catheters, guidewires and other accessories.

A common technique for accomplishing the non-disruptive removal of the delivery device involves slitting or otherwise cutting the catheter over the lead using a small blade known as a slitter. A typical catheter used in this technique is designed such that the force required to slit the sheath is as low and as consistent as possible. However, the hub of the delivery catheter typically requires considerably more force to slit through than is required for the shaft. That is, when slitting the catheter, the user begins by generating enough force to slit through the hub. As the slitter transitions from the hub to shaft, this force is excessively high and results in an acceleration or jerk. In the context of an implantable cardiac lead, if this jerk is severe, it may tear the cardiac tissue or disrupt lead placement, which results in a major procedural delay. Similarly, disruption of other cardiac surgical tools, such as an inner catheter, may cause damage to cardiac tissue or major procedural delays.

There is a need in the art for a slittable delivery device for an implantable cardiac electrotherapy lead or other cardiac surgical tool that will reduce or eliminate the hub-to-shaft transitional jerk and reduce the potential for lead or cardiac surgical tool displacement or dislodgement during removal of a delivery device. There is also a need in the art for a method of manufacturing such a delivery device.

BRIEF SUMMARY OF THE INVENTION

Disclosed herein is a slittable delivery device for the delivery of a cardiac surgical device. In one embodiment, the delivery device includes a hub and a shaft integrated into the hub. The shaft of the sheath forms at least a segment of the circumferential surface of the hub. The delivery device may also include a hemostasis valve contained substantially within the hub and a cap on a proximal end of the hub. The cap may include an opening in the cap extending radially outward from a point near a radial center of the cap through a circumferential edge of the cap. The cardiac surgical device may be at least one of an implantable cardiac electrotherapy lead, an inner catheter or sheath, a stylet, a guidewire, a sensor device, or any other device or accessory typically delivered via an introducer sheath or catheter.

Disclosed herein is a slittable delivery device for the delivery of a cardiac surgical device. In one embodiment, the delivery device includes a shaft and a hub coupled to the shaft. The shaft is formed of at least a first material. The hub includes a wall including a first wall segment and a second wall segment. The first wall segment includes at least the first material and the second wall segment includes at least a second material that is at least one of harder and more rigid than the first material. In some embodiments, the second material is at least one of softer and less rigid than the first material. The cardiac surgical device may be at least one of an implantable cardiac electrotherapy lead, an inner catheter or sheath, a stylet, a guidewire, a sensor device, or any other device or accessory typically delivered via an introducer sheath or catheter.

Disclosed herein is a slittable delivery device for the delivery of a cardiac surgical device. In one embodiment, the delivery device includes a shaft, a hub coupled to a proximal end of the shaft, and a consistent slitting medium extending generally the lengths of the shaft and hub. The cardiac surgical device may be at least one of an implantable cardiac electrotherapy lead, an inner catheter or sheath, a stylet, a guidewire, a sensor device, or any other device or accessory typically delivered via an introducer sheath or catheter.

Disclosed herein is a slittable delivery device for the delivery of a cardiac surgical device. In one embodiment, the device includes a shaft and a hub coupled to a proximal end of the shaft and including a wall. The shaft forms a longitudinally extending strip of the wall generally an entire longitudinal length of the wall. The cardiac surgical device may be at least one of an implantable cardiac electrotherapy lead, an inner catheter or sheath, a stylet, a guidewire, a sensor device, or any other device or accessory typically delivered via an introducer sheath or catheter.

Disclosed herein is a slittable delivery device for the delivery of a cardiac surgical device. In one embodiment, the device includes a shaft and a hub coupled to a proximal end of the shaft. The material of the shaft extends an entire length of the shaft and hub uninterrupted and fully exposed for slitting by a slitting tool. The cardiac surgical device may be at least one of an implantable cardiac electrotherapy lead, an inner catheter or sheath, a stylet, a guidewire, a sensor device, or any other device or accessory typically delivered via an introducer sheath or catheter.

Disclosed herein is a method of manufacturing a slittable delivery device for the delivery of a cardiac surgical device. In one embodiment, the method includes: providing a shaft; and forming a hub on a proximal end of the shaft, wherein a portion of the shaft forms a longitudinally extending segment of a circumferentially extending wall of the hub.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
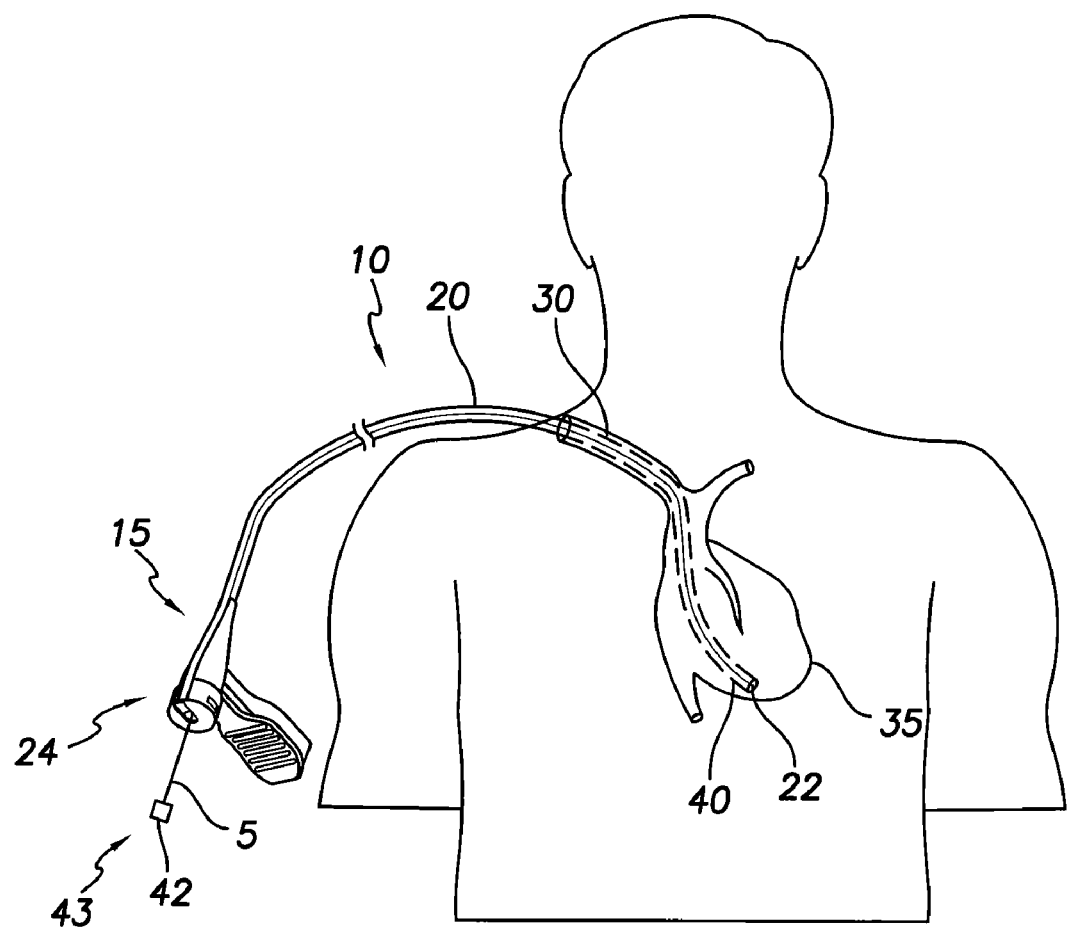
FIG. 1 is a diagrammatic view showing a slittable delivery device according to the present disclosure as it may be used for delivery of a cardiac surgical device.

The present disclosure describes a slittable delivery device 10 for a cardiac surgical device 5, e.g. an implantable medical lead, an inner catheter or sheath, a stylet, a guidewire, a sensor or other accessories or devices typically delivered via a catheter or sheath. The delivery device 10 may be a delivery catheter or sheath 10 having a tubular shaft 20 and a hub 15 on a proximal end 24 of the device 10. The delivery device 10 includes a lumen extending the length of the delivery device 10 and which provides a passageway for the surgical device 5 to enter the body, for example, the heart during implantation of a lead 5. Upon placement of the surgical device 5, the delivery device 10 is removed from about the surgical device 5 via slitting or splitting of the delivery device 10 along its length.

In one embodiment, the tubular shaft 20 is integrated into the hub 15 such that a wall 7 of the shaft 20 forms a longitudinally extending strip of the wall 125 of the hub 15 the entire longitudinal length of the hub wall 125 from a most proximal end 16 of the hub 15 to a most distal end 17 of the hub 15. Thus, in one embodiment, the material forming the shaft 20 may be considered to extend the entire length of the device 10 uninterrupted and fully accessible to a cutting/slicing/splitting tool 45, even through the entire length of the hub 15. When using the tool 45 to slit the delivery device 10 along its entire length, including the full lengths of the shaft 20 and hub 15, the tool 45 may encounter only the shaft material without encountering hub material, enabling the delivery device 10 to be slit and removed from about the cardiac surgical device 5 without disrupting the surgical device 5. The hub 15 with its integrated longitudinally extending shaft strip 23 reduces the hub-to-shaft transitional jerk that may occur with other delivery devices, thereby reducing the complications associated with dislodging the placed lead or other cardiac surgical device, such as increased procedure time or damage to cardiac tissue.

In one embodiment, a hemostasis valve 25 is integrated into the hub 15. An integrated hemostasis valve 25 may further reduce the time required for, and risk associated with, the procedure because preparation steps, such as splitting or otherwise removing the valve 25 prior to removal of the device 10, are not required.

For a general discussion of a slittable delivery device 10 utilized to deliver a cardiac surgical device 5, reference is first made to FIG. 1, which is a diagrammatic view of the delivery device 10 as it may be used during delivery of a cardiac surgical device 5, such as an implantable cardiac electrotherapy lead. The following discussion is given in the context of the cardiac surgical device 5 being a lead 5. However, the cardiac surgical device 5 may be any other type of device 5, including, for example, inner sheaths or catheters, guidewires, stylets, sensors, etc. The delivery of such surgical devices 5 via the delivery device 10 will be similar to that described below with respect to the delivery of a lead 5.

As previously mentioned and as can be understood from FIG. 1, the delivery device 10 may be a delivery catheter or sheath 10 having a tubular shaft 20 and a hub 15 on a proximal end 24 of the device 10. The hub 15 may include an integral hemostasis valve 25. During a lead implantation procedure, for example, the tubular shaft 20 is inserted into the patient's heart 35 via the subclavian vein 30 or other appropriate entry point.

Once the shaft 20 is in position, a cardiac surgical device 5 may be inserted therethrough. For example, once the shaft 20 is in position, a lead 5 may be inserted through the hemostasis valve 25 in the hub 15 and through the lumen of the shaft 20 so the lead tip 40 at the distal end of the lead 5 may be guided into position in the heart 35.

The lead 5 includes a proximal end 43. In one embodiment, the proximal end 43 of the lead 5 includes an electrical connector 42 for mechanically and electrically coupling the lead proximal end to a pulse generator, such as a pacemaker or ICD. The electrical connector 42 is of a size that prevents the delivery device 10 from being proximally withdrawn from about the lead 5. The length of the lead 5 may present an equal hindrance. Once the lead 5 is implanted or placed into position, as appropriate, the device 10 may be slit to allow the delivery device 10 to clear the connector 42 or proximal end 43 as the delivery device 10 is removed from about the lead 5.

As mentioned above and described in more detail below, the material forming the shaft 20 extends into the hub 15 to form at least a longitudinal strip of the hub wall 125. Thus, the slit path for slitting the entire delivery device 10, including the entire shaft 20 and entire hub 15, extends along shaft material and does not encounter hub material, or at least any significant amount of hub material. With respect to the slitting path 23, the delivery device 10 has no hub-to-shaft transition, resulting in a delivery device 10 that may be slit with low and consistent slit forces along the entire length of the delivery device 10, substantially reducing, if not completely eliminating, the transition jerk normally associated with slitting through the hub-to-shaft transition of devices known in the art. Advantageously, the chance of dislodging or disrupting the position of the implanted lead 5 is reduced or eliminated. Additionally, because the shaft is integrated into the hub, the delivery device 10 does not require removal of the hub in order to slit the shaft. In some embodiments, the hub 15 may include an integrated valve and cap configured to be slit, thereby increasing the efficiency and reducing the risk associated with employing the device 10.

Figure 2:
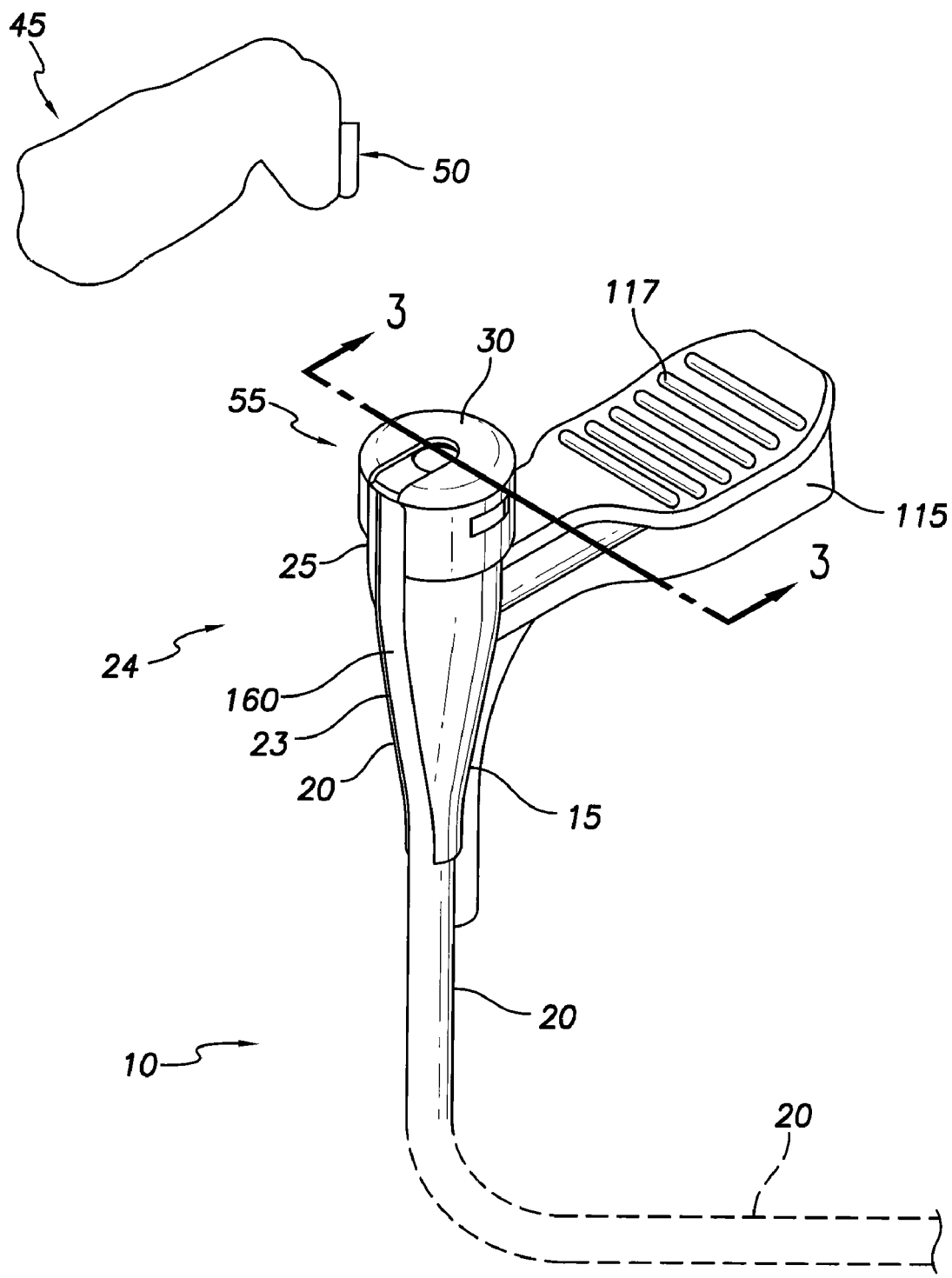
FIG. 2 is an embodiment of the slittable delivery device of FIG. 1, wherein a slitting tool is also shown.
Figure 3:
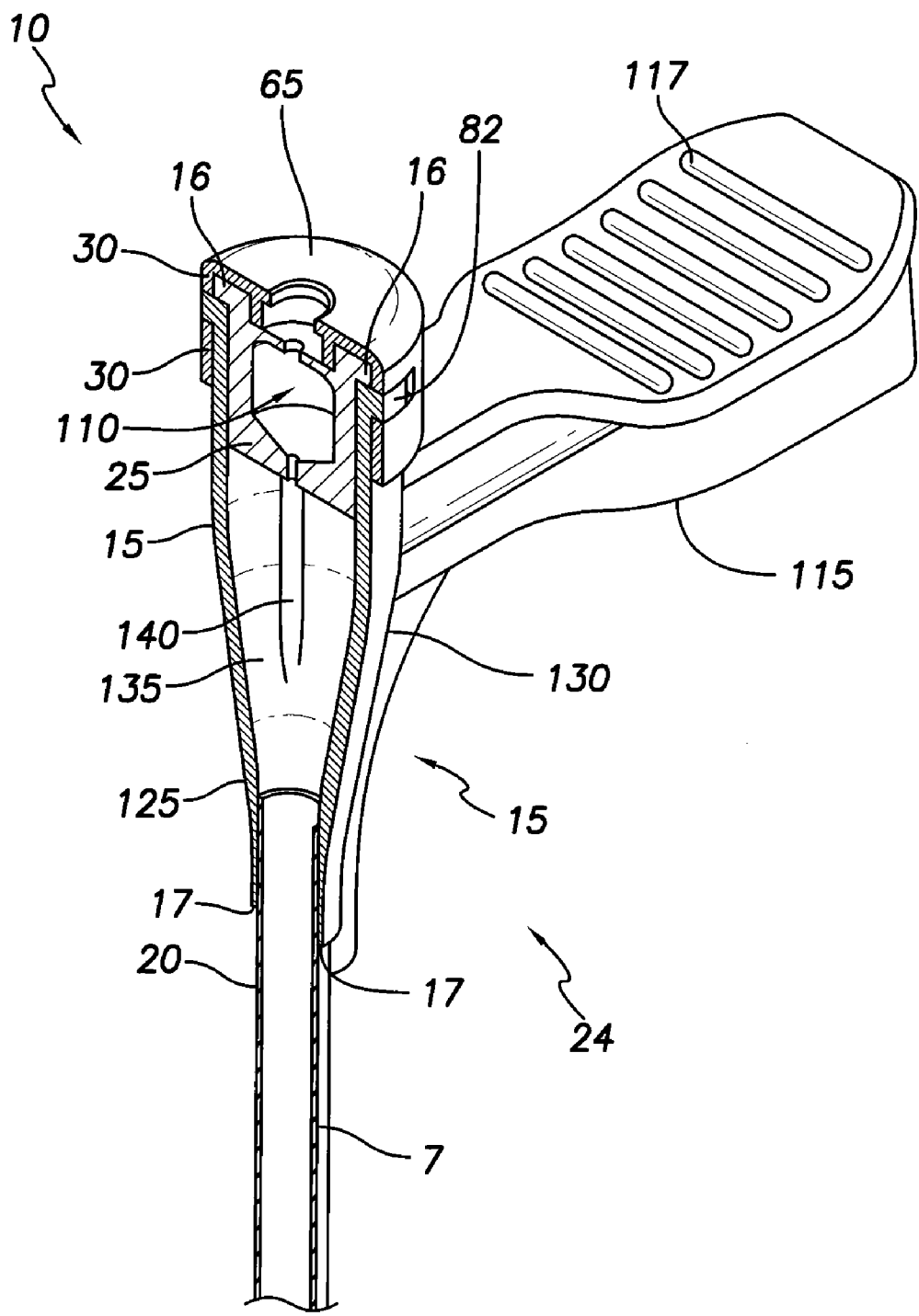
FIG. 3 is a cross-sectional elevation of the device as taken along section line 3-3 of FIG. 2.
Figure 6A:
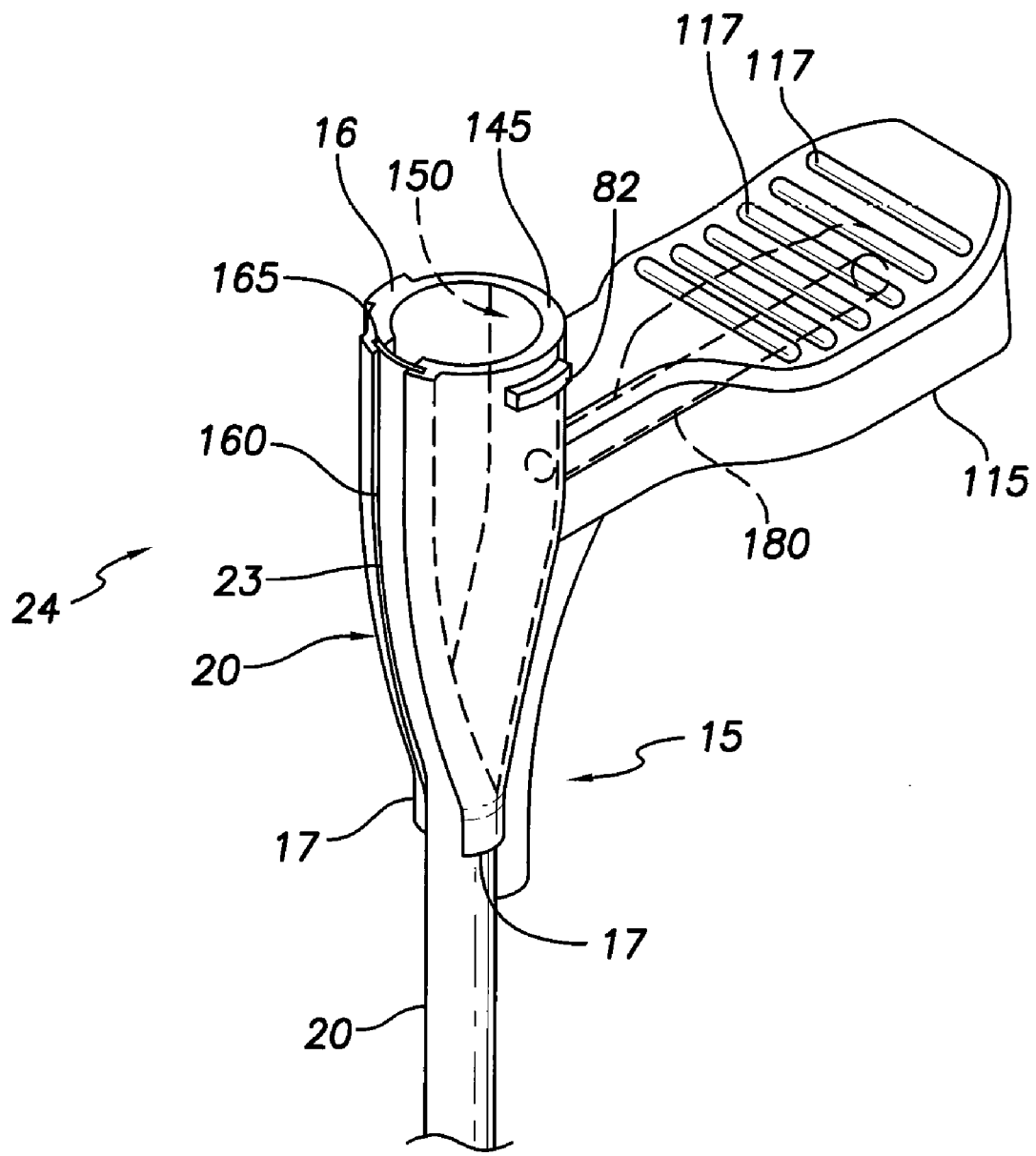
FIG. 6A is a transparent view of one embodiment of the hub and sheath of FIG. 2, wherein the valve and cap are hidden for clarity purposes.
Figure 6B:
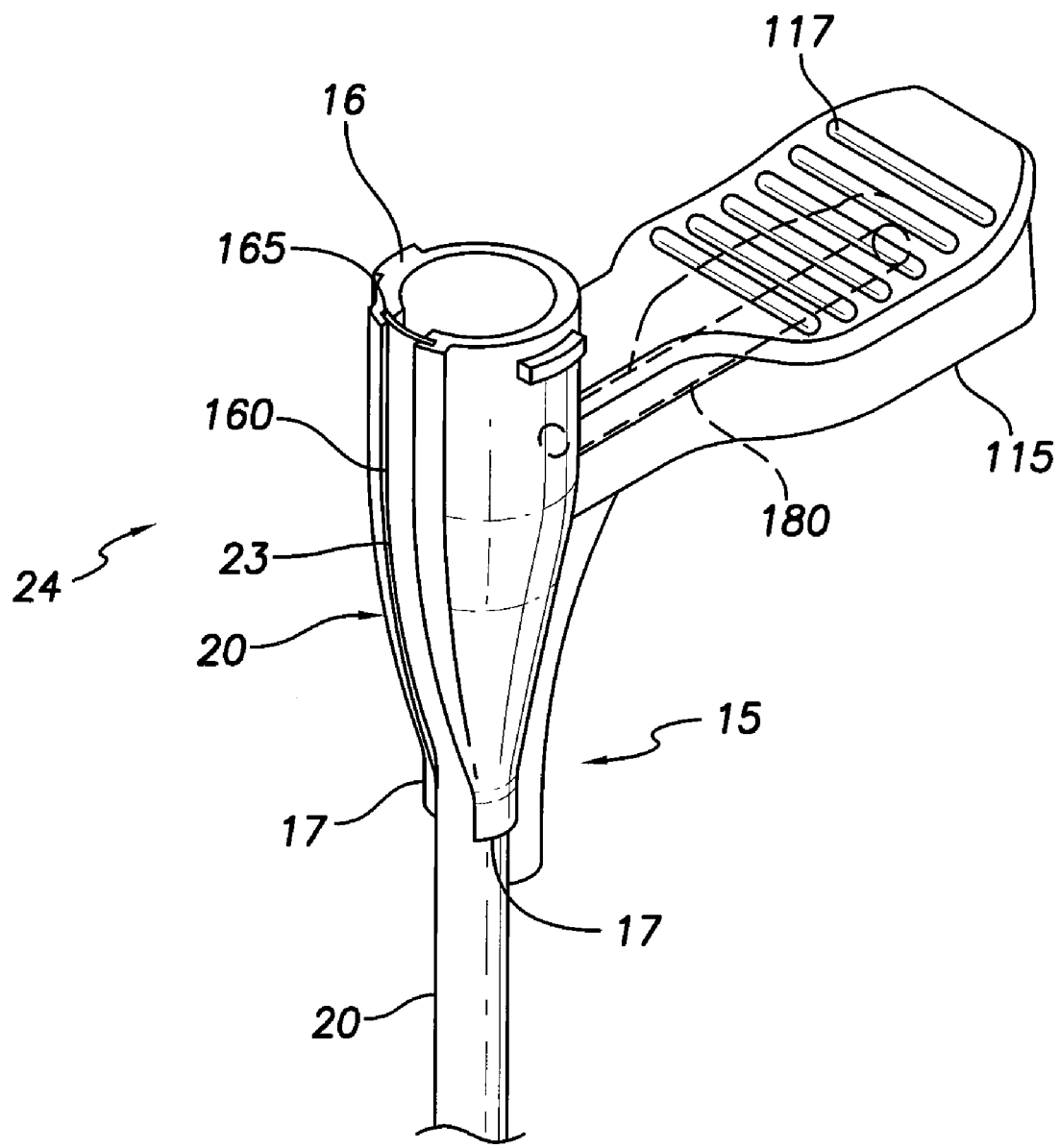
FIG. 6B is a transparent view of a second embodiment of the hub and sheath of FIG. 2, wherein the valve and cap are hidden for clarity purposes.
Figure 7A:
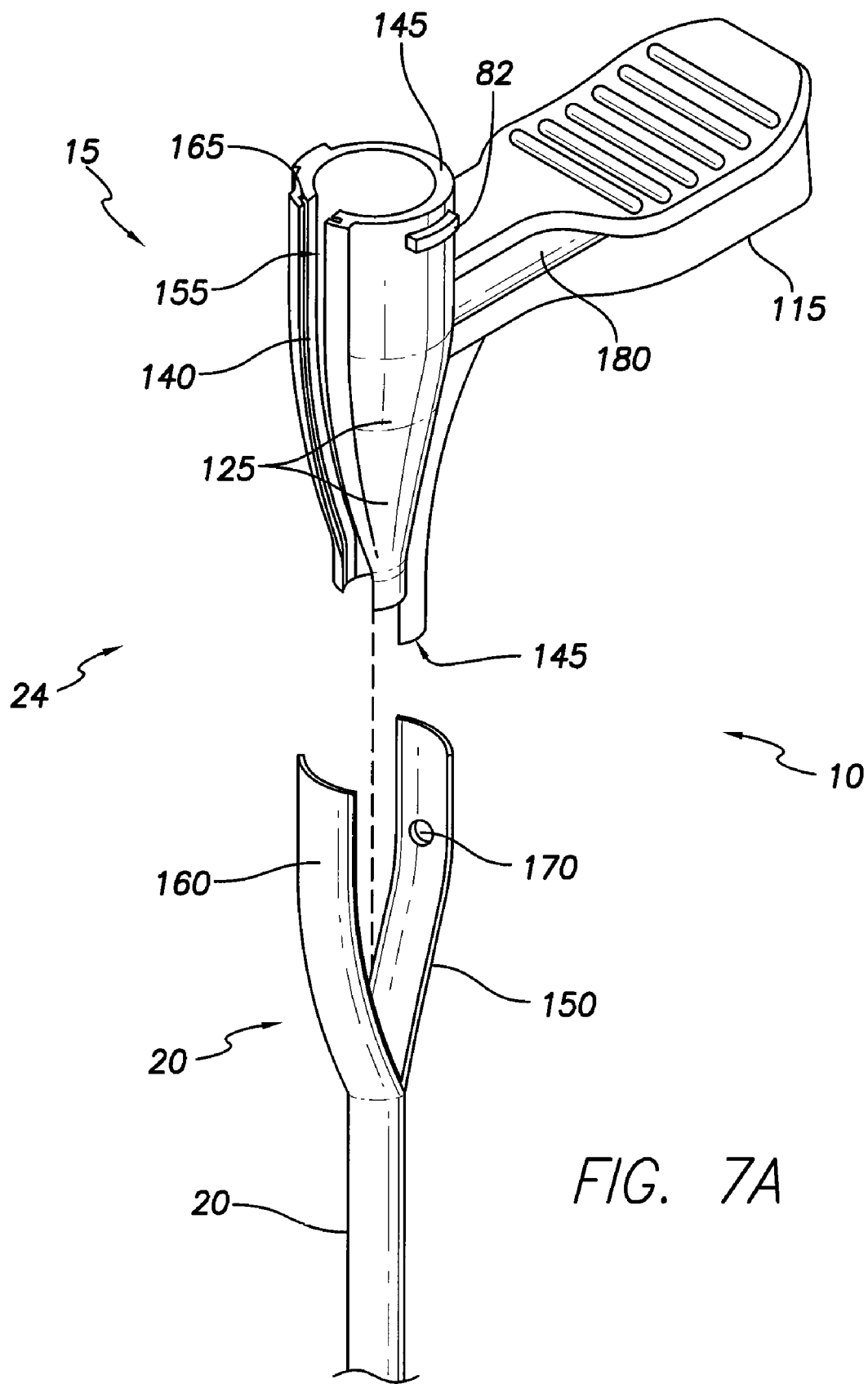
FIG. 7A is an exploded view of one embodiment of the delivery device of FIG. 6A.
Figure 7B:
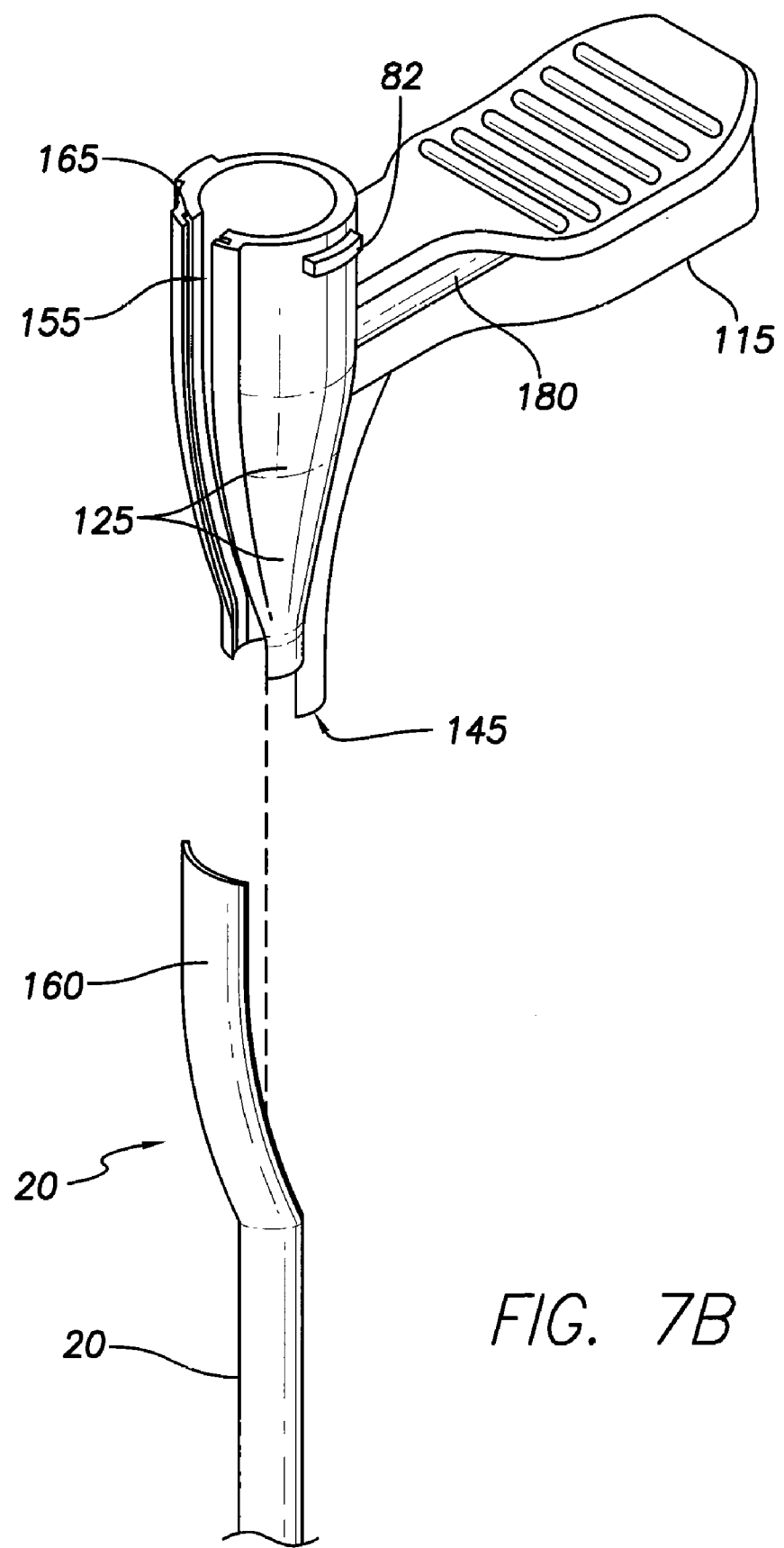
FIG. 7B is an exploded view of a second embodiment of the delivery device of FIG. 6B.
Figure 8A:
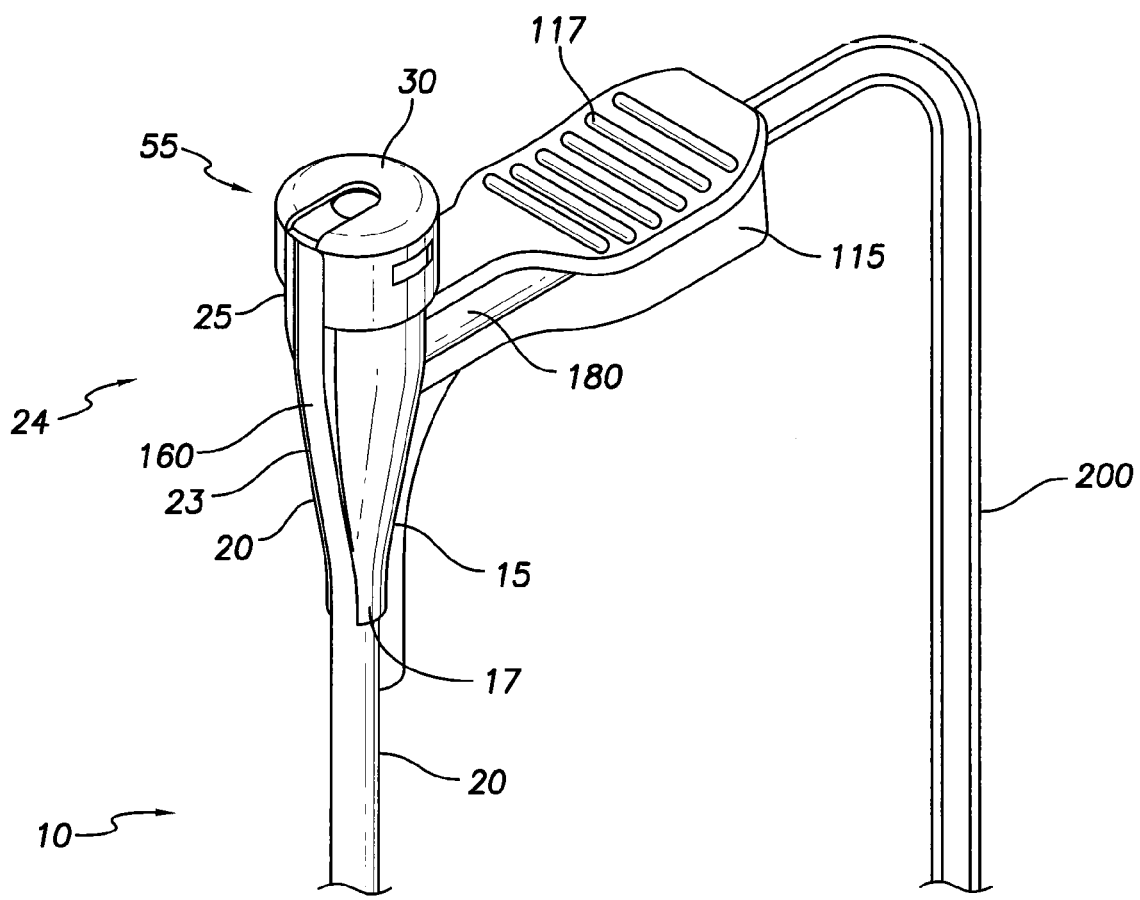
FIG. 8A is an embodiment of the slittable delivery device of FIG. 1, wherein a side port extension tube is also shown.
Figure 8B:
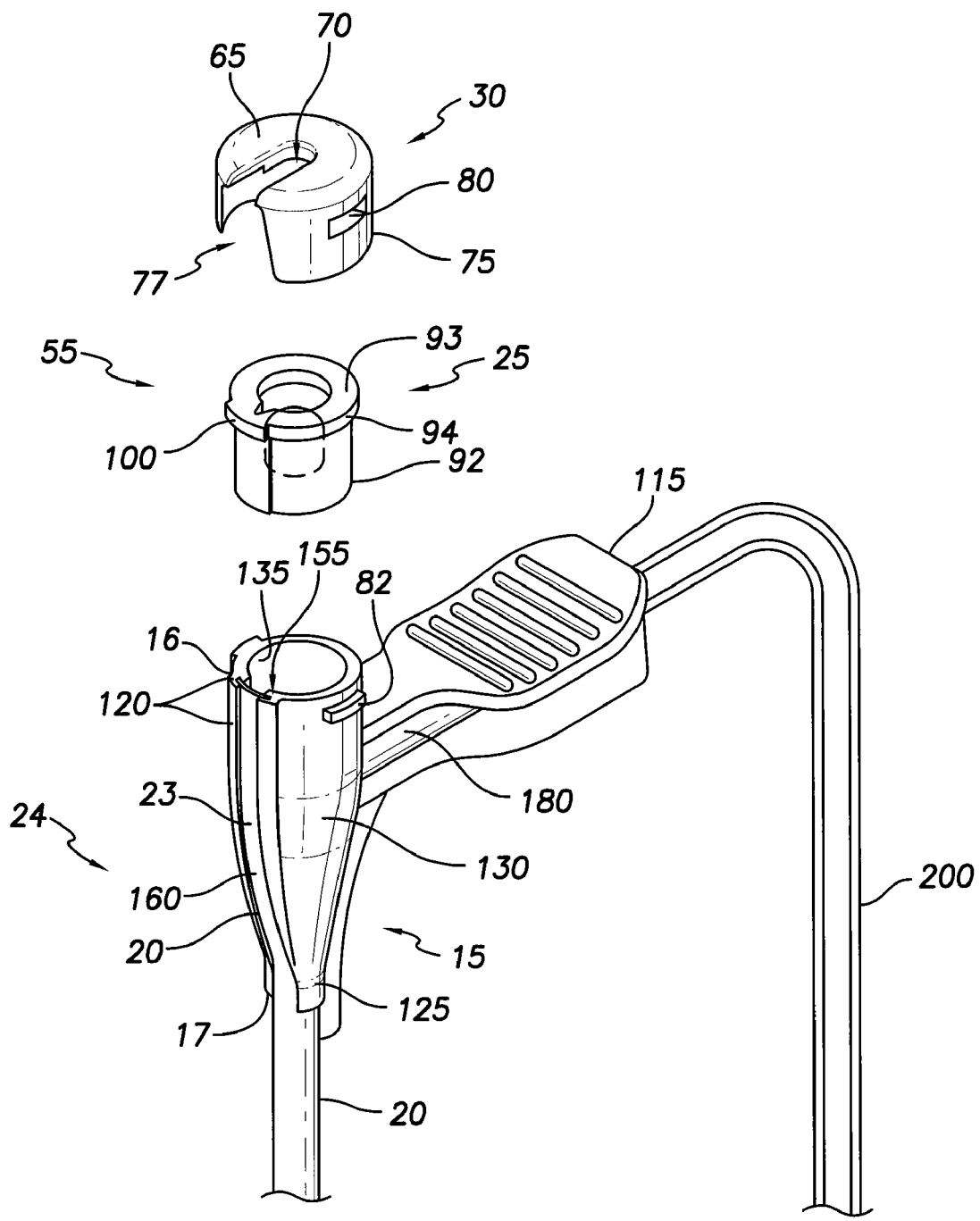
FIG. 8B is a partially exploded view of the slittable delivery device of FIG. 8A.

For a detailed discussion of the slittable delivery device 10 and the components of the delivery device 10, reference is now made to FIGS. 2-8B. FIG. 2 is an isometric view of the slittable delivery device 10 and a slitter 45, and FIG. 3 is a cross-sectional elevation of the delivery device 10 as taken along section line 3-3 of FIG. 2. FIGS. 4A and 4B are partially exploded views of some embodiments of the hub end 24 of the delivery device 10, and FIGS. 5A and 5B are isometric views of some embodiments of the valve 25. FIGS. 6A and 6B are transparent views of some embodiments of a hub 15 and sheath 22, and FIGS. 7A and 7B are exploded views of some embodiments of the hub 15 and sheath 22 of FIGS. 6A and 6B, respectively. FIG. 8A is an embodiment of the slittable delivery device of FIG. 1, wherein a side port extension tube is also shown. FIG. 8B is a partially exploded view of the slittable delivery device of FIG. 8A.

As can be understood from FIGS. 2-4B, the slittable device 10 includes the shaft 20 and the hub 15. In some embodiments, the device 10 further includes a valve 25 and a cap 30, wherein the cap 30 retains the valve 25 inside the hub 15 to form a hub with an integral hemostasis valve.

As indicated in FIG. 2, the device 10 may also include a slitting tool 45 for slitting/splitting/cutting the device 10, including the shaft 20 and the hub 15. The slitter 45 includes a blade 50 or other suitable cutting mechanism. In alternative embodiments, the slittable delivery device 10 may be slit with another suitable cutting or slitting tool.

As shown in FIGS. 2-4B, the proximal end 24 of the device 10 includes the hub 15, which is mounted on the proximal end of the shaft 20. The hub 15 includes a proximal end 16 and a distal end 17. The hub 15 may be configured such that the hub proximal end 17 may receive and couple with a hemostasis valve such as those commonly known in the art. Alternatively, the hub 15 may be equipped with an integral hemostasis valve 25 located within the hub 15 and maintained in place via a cap 30 configured to couple with the hub proximal end 16.

Figure 4A:
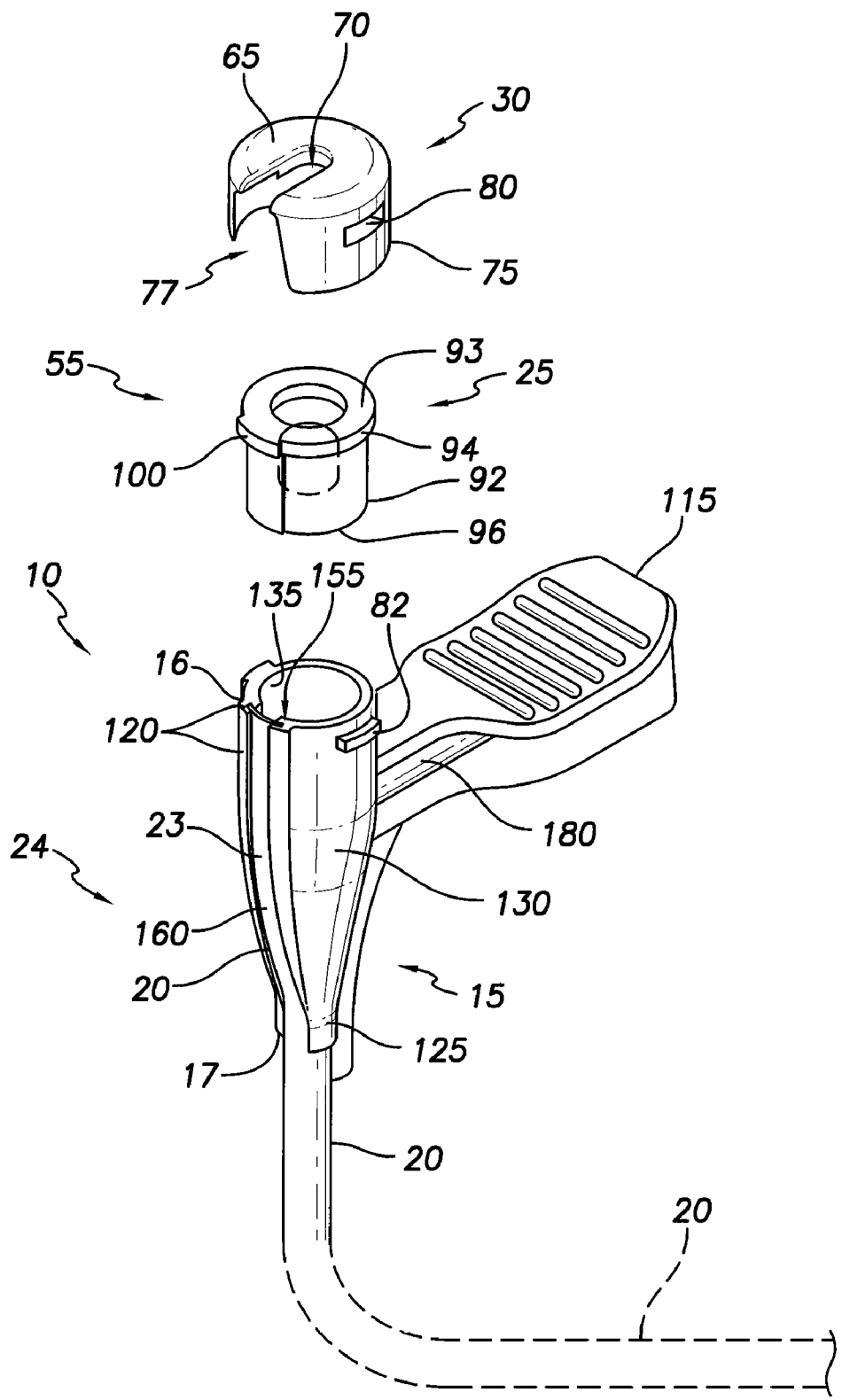
FIG. 4A is a partially exploded view of one embodiment of the hub end of the delivery device of FIG. 1.
Figure 4B:
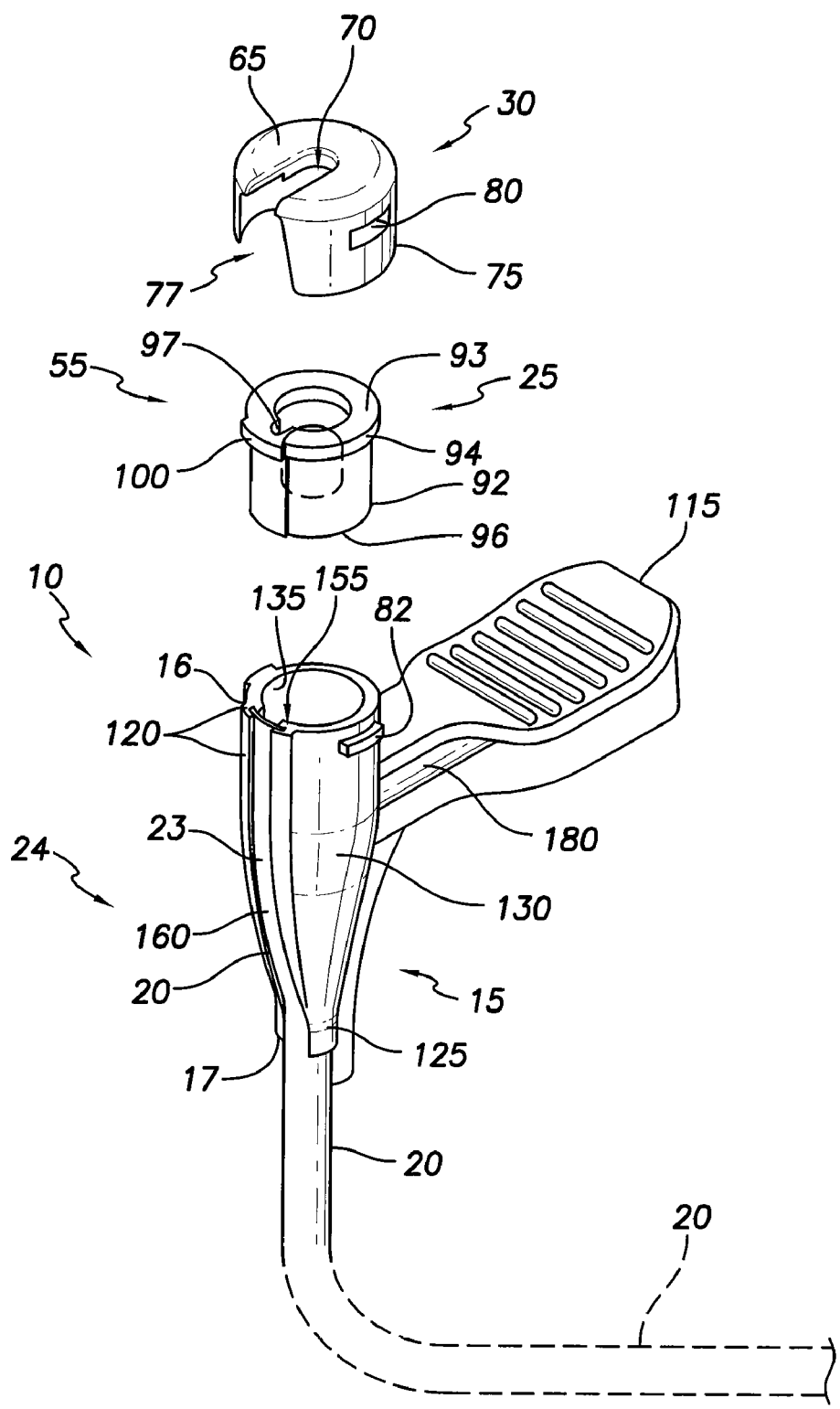
FIG. 4B is a partially exploded view of a second embodiment of the hub end of the delivery device of FIG. 1.

As indicated in FIGS. 2, 4A and 4B, the cap 30 is generally an open-ended cylindrical shape and includes a proximal or surgical device receiving face 65 and a lateral generally cylindrical wall 75. The cap 30 is configured to generally receive the hub 15, thereby partially enclosing the proximal face of the valve 25 and maintaining the valve within the hub 15 to create a fluid tight seal. The cap 30 may be made of a generally rigid, hard material, for example, acrylonitrile-butadiene-styrene ("ABS"), polyether block amides ("PEBAX"), high density polyethylene ("HDPE"), polycarbonate, nylon, or etc.).

As indicated in FIGS. 2, 4A and 4B, the surgical device receiving face 65 of the cap 30 is generally circular and includes a U-shaped opening 70. The U-shaped opening 70 is configured to receive the distal end of the cardiac surgical device 5. The U-shaped opening 70 also exposes a portion of the valve 25 such that a slittable valve 25 may also be slit during removal of the device 10. Also, the U-shaped opening 70 allows for the cap 30 to be removed from about the cardiac surgical device 5 once the surgical device 5 is implanted or otherwise positioned. That is, the cap 30, which may be coupled to the valve 25, may be removed from about the surgical device 5 during or after slitting of the delivery device 10.

As shown in FIGS. 2, 4A and 4B, the wall 75 of the cap 30 includes an arcuate opening 77. The arcuate opening 77 nearly intersects the proximal face 65 of the cap 30 at the open end of the U of the U-shaped opening 70 to merge with the U-shaped opening 70. The arcuate opening 77 is configured to expose a proximal portion of the hub 15 and the shaft 20 and, more specifically, to expose the slit path or strip 23 extending the length of the hub 15, thereby allowing the tool blade 50 to access the slit strip 23. In one embodiment, the arcuate opening 77 may also expose a portion of a slittable valve, thereby aiding in slitting of a slittable valve.

As can be understood from FIGS. 2-4B, the wall 75 of the cap 30 also includes tab receiving openings 80. The openings 80 are configured to receive hub tabs 82 defined on the outer circumference of the hub 15, thereby forming a bayonet lug type connection arrangement. In one embodiment, the openings 80 are rectangular. In other embodiments, the openings 80 may be a different shape, such as circular or other suitable shape as needed to conform to the tabs 82 defined on the hub 15. In one embodiment, there are two tab receiving openings 80. In alternative embodiments, there may be less than two openings 80 or there may be more than two openings 80.

In some embodiments, the delivery device 10 includes an integrated or internal hemostasis valve 25 configured to be received in the hub 15 and maintained in place by the cap 30, as discussed above. In other embodiments, the delivery device 10 does not include the integrated hemostasis valve 25 or cap 30. Instead, the proximal end 16 is configured to receive an external hemostasis valve as commonly used in the art.

As shown in FIGS. 4A-5B, in some embodiments, the integral hemostasis valve 25 includes an outer housing or body component 92 and an inner valve component 90. The valve 25 is generally cylindrical and is configured to mate with and be received within the hub 15, thereby creating a fluid tight seal. In one embodiment, the valve 25 is formed from a generally resilient, soft material, e.g., (e.g. silicone rubber or other elastomer).

Figure 5A:
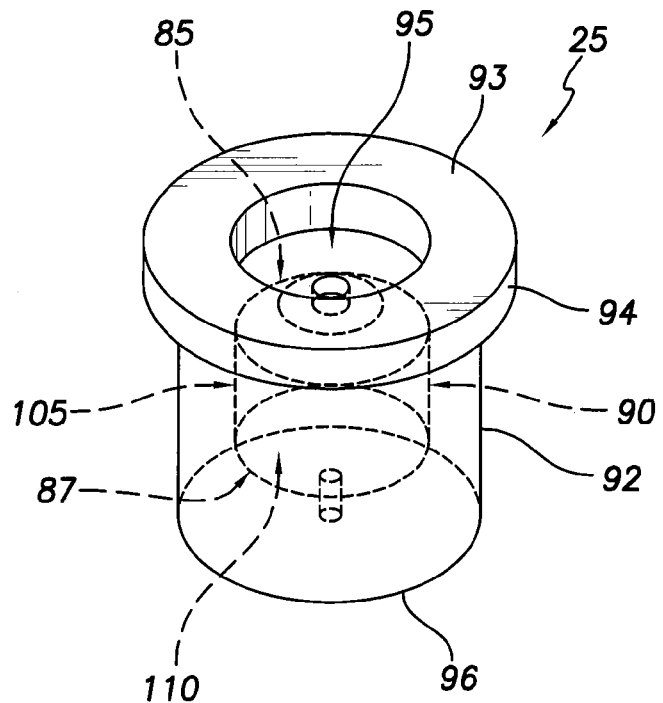
FIG. 5A is an isometric view of one embodiment of the valve of FIG. 4A.
Figure 5B:
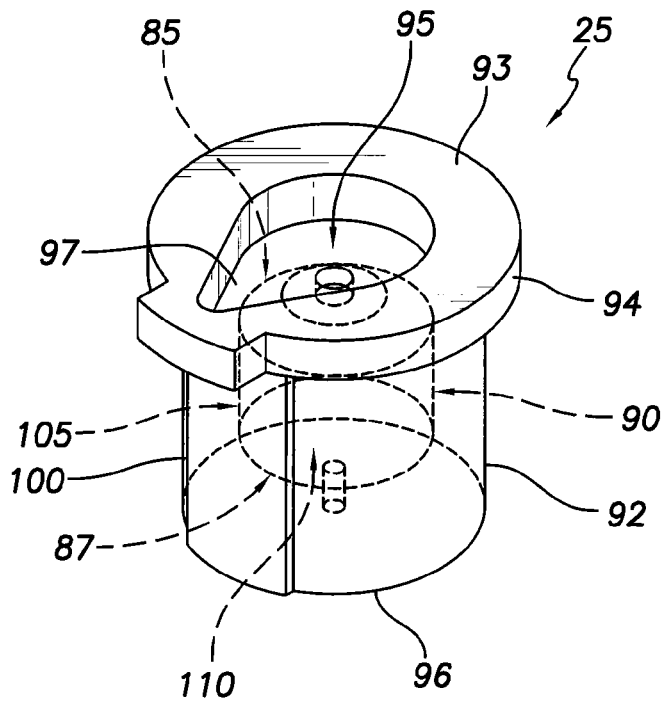
FIG. 5B is an isometric view of a second embodiment of the valve of FIG. 4B.

As indicated in FIGS. 4A-5B, the housing 92 of the valve 25 includes a cap side 93 that is configured to matingly receive the cap 30 and a hub side 96 that is configured to be received in the hub 15. The cap side 93 of the housing 92 is generally circular or disc-shaped and includes an opening 95 defined therein. In one embodiment, the circumference of the cap side 93 of the housing 92 is greater than the circumference of the housing 92, thereby forming a rim or lip 94. In alternative embodiments, the circumference of the cap side 93 is approximately equal to the circumference of the housing 92. In one embodiment, as shown in FIGS. 4B and 5B, the opening 95 may include a v-notch 97, which may help to align the slitter and provide for ease of slitting.

As can be understood from FIGS. 4A, 4B and 5B, in some embodiments, the outer circumference of the cap side 93 of the housing 92 may include a valve tab 100. The valve tab 100 extends from the outer circumference of rim 94 of the cap side 93 on approximately the same plane as the cap side. In one embodiment, as shown in FIG. 5B, the valve tab 100 extends from the outer circumference of rim 94 of the cap side 93 on approximately the same plane as the cap side 93 and extends along a portion of the outer circumference of the housing 92 of the valve 25 between the cap side 93 and the hub side 96. Referring now to FIGS. 4A-5B, in some embodiments, the valve 25 may be coupled to the cap 30 and together, the valve 25 and cap 30 are coupled to the hub 15. The valve tab 100 may provide a feature for grasping to insert the valve into the hub or to facilitate the removal from the hub during manufacture. The valve tab 100 may also help to facilitate the seal between the cap 30, valve 25 and hub 15. As indicated in FIGS. 2 and 5A, in an alternative embodiment, the outer circumference of rim 94 of the cap side 93 of the housing 92 of the valve 25 may not include a valve tab 100.

As shown in FIGS. 4A-5B, the opening 95 in the face of the cap side 93 of the valve 25 provides an entryway or passageway leading to the inner valve component 90. The inner valve component 90 includes resilient members 85, 87 and a wall 105. The resilient members 85, 87 and the wall 105 define a chamber 110 through which a cardiac electrotherapy lead or other cardiac surgical device may pass during placement of the lead or other device into the heart. The resilient members 85, 87 include a slit or other opening that may bias closed around a surgical device 5 extending through the inner valve component 90, creating a fluid tight seal about the surgical device 5.

As shown in FIGS. 2-4B and 6A-7B, the proximal end 24 of the delivery device 10 includes a hub 15 with an integrated shaft 20 forming a longitudinally extending hub splitting strip 23 in the hub wall 125. As can be understood from FIGS. 6A-7B, in some embodiments, to assist in the integration of the shaft 20 into the hub 15 during manufacture, the proximal end of the shaft 20 may be split or divided along a longitudinal centerline prior to being molded or formed into the hub. One of the shaft segments resulting from the longitudinal dividing of the shaft proximal end is an exposed portion 160 and the other an unexposed portion 150 imbedded within the material forming the hub 15. As indicated in FIGS. 6B and 7B, in some embodiments, the proximal end of the shaft 20 includes only a single shaft segment, the exposed portion 160.

As illustrated in FIGS. 6A-7B, the unexposed portion 150 and exposed portion 160 of the shaft 20, if present, are integrated into the hub 15 such that the exposed portion 160 is aligned with the hub opening 155 and forms at least a segment of the circumferential surface of the hub 15, as discussed in more detail below. In one embodiment, the proximal end of the shaft 20 extends to the proximal end 16 of the hub 15. In other embodiments, the proximal end of the shaft 20 may extend to an alternative location within the hub 15 somewhere between the hub proximal end 16 and hub distal end 17. The shaft 20 may be formed of polytetrafluoroethylene ("PTFE"), PEBAX, Nylon, polyurethane, fluorinated ethylene propylene ("FEP") or etc. or a combination of these materials supported by a reinforcement braid pattern.

As indicated in FIGS. 4A and 4B, and 6A-8B, the hub 15 may include a handle 115 with a portal 180 extending from the interior of the hub 15 to daylight at the free end of the handle 115. As shown in FIG. 7A, the unexposed portion 150 of the shaft 20 may include a portal opening 170. The portal opening 170 generally corresponds to the opening in the interior of the hub formed by the portal 180 in the hub handle 115.

As shown in FIGS. 3, 4A, 4B, and 6A-8B, the hub 15 includes a body 125 which may be a generally conical wall with an outer circumferential surface 130 and an inner circumferential surface 135. The outer surface 130 of the body 125 may include the hub tabs 82 and the handle 115. The hub tabs 82 are configured to be received by the hub receiving openings 80 defined in the cap 30, thereby creating a seal between the valve 25, cap 30 and the hub 15. The hub body or wall 125 may be formed of a generally rigid, hard material, for example, acrylonitrile-butadiene-styrene ("ABS"), polyether block amides ("PEBAX"), high density polyethylene ("HDPE"), polycarbonate, nylon, or etc.).

In one embodiment, the handle 115 includes a portal 180 and ridges 117 that provide a gripping surface. The portal 180 provides a passageway into the hub 15 via the handle 115 and the portal opening 170 in the shaft 20 for the delivery of fluids, such as fluoroscopy contrasts, etc. into the lumen of the device 10. As shown in FIGS. 8A and 8B, an extension tube 200, such as a PVC extension tube with a three-way stopcock valve, may be coupled to the portal 180 and may serve to deliver the fluids. The handle 115 may provide leverage or stability for the device 10 during delivery of the cardiac surgical device 5 or slitting of the delivery device 10.

As indicated in FIG. 3, in one embodiment, the inner circumference 135 of the body 125 of the hub 15 includes raised portions 140 configured to generally abut the distal end of the valve 25 and impede or stop the valve 25 from extending distally beyond a desired point in the hub 15. In other embodiments, the hub 15 may not include raised portions 140, but rather the shape or contours of the hub 15 may impede or prevent the valve 25 from distally extending beyond a desired point in the hub 15.

As can be understood from FIGS. 6A and 7A, in one embodiment, a void or space 145 is defined between the inner circumference 135 and outer circumference 130 of the hub 15. The unexposed portion 150 of the shaft 20 is received in the void or space 145. More specifically, in one embodiment, during the manufacturing process when the hub wall 125 is formed (e.g., via insert or injection molding) about the unexposed portion 150, the portion 150 defines the void or volume in the hub wall 125 in which the portion 150 resides.

As shown in FIGS. 2, 3, 4A-4B, and 6A-8B, in some embodiments, the hub 15 is generally a flat-bottomed conical shape. The body or wall 125 of the hub 15 includes slots 165 and a hub opening 155 configured to receive an exposed portion 160 of the shaft 20. The hub opening 155 may be a longitudinal gap or slot 155 defined in and extending the length of the hub wall 125 from the proximal hub end 16 to the distal hub end 17. The exposed portion 160 of the shaft 20 is received in the hub opening 155 such that the exposed portion 160 forms a longitudinally extending segment of the hub wall 125, including longitudinally extending segments of the inner and outer surfaces 130, 135 of the hub wall 125.

To secure the exposed portion 160 in place such that it forms a longitudinal segment of the hub wall 125, the lateral edges of the exposed portion 160 are received in the slots 165 bordering each wall edge of the hub wall 125 defining the hub opening 155. Similar to the creation of the void space 145 with respect to the unexposed portion 150, in one embodiment, during the manufacturing process when the hub wall 125 is formed (e.g., via insert or injection molding) about the lateral edges of the exposed portion 160, the portion 160 defines the slots 165 in the hub wall 125 in which the lateral edges of the portion 160 reside.

As can be understood from FIGS. 2-4B and 6A-8B, the shaft 20 is integrated into the hub 15 such that the shaft 20 forms a longitudinally extending segment of the hub wall 125. In one embodiment, this longitudinally extending segment of the hub wall 125 provides a slitting path extending the full length of the delivery device 10 and formed of shaft material and no hub material at all or of any significant amount. This configuration allows the delivery device 10 to be slit along its entire length without removal of the hub 15 and without a transitional jerk. Thus, in one embodiment, a physician may slit through the length of the delivery device 10 and encounter only a single slittable medium with low and consistent slit forces, thereby reducing or eliminating the shaft-to-hub transitional jerk and reducing the likelihood of disrupting the placement of the cardiac surgical device 5 upon removal of the delivery device 10.

In an alternative embodiment, as shown in FIG. 4A, the body 125 of the hub 15 may include ridges 120 extending along the edges of the hub opening 155. The ridges 120 include the slots 165, which, as discussed above, are configured to receive the lateral edges of the exposed portion 160 of the shaft 20. That is, the shaft 20 is integrated into the hub 15 at the hub opening 155 and is received in the ridges 120 with slots 165 such that the shaft 20 forms at least a longitudinal segment of the hub wall 125.

As can be understood from FIGS. 2, 3 and 6A-6B, in some embodiments, the hub opening 155 extends the length of the hub 15 and provides a small channel through which the shaft 20 may be slit. A small channel allows the hub to retain its radial strength and also provides a directional window or visual indicator to direct the physician to the slit channel. In other embodiments, the hub 15 may have a differently shaped hub opening 155 as long as the opening 155 accommodates extension of the shaft 20 into the hub 15 such that the shaft 20 may comprise at least a longitudinal segment of the hub wall 125.

In one embodiment, the hub may be insert injection molded or injection molded around the shaft. In an alternative embodiment, the hub may be machined or molded and then the shaft may be assembled into the hub. The valve and cap may also be assembled into or onto the hub. Once assembled, the delivery device 10 may be utilized in a medical procedure to implant or otherwise place a cardiac surgical device 5.

As can be understood from FIG. 2, and with reference to FIG. 1, the delivery device 10 is generally configured to receive a lead or other cardiac surgical device 5 at the proximal end 17 of the device 10, and the lead or other surgical device 5 may be guided through the lumen of the shaft 20 to the implant or desired location in the heart 35. Once the lead is implanted at the desired electrotherapy implant location or the surgical device is placed at the desired location, the delivery device 10 may be slit with a slitter 45 or other cutting tool and withdrawn from about the surgical device 5. As discussed above, the cap 30 and valve 25 may be coupled to the hub 15. In some embodiments, the arcuate opening 77 in the cap 30 is configured to allow passage of the slitter blade through the cap 30 and valve 25 such that removal of the cap 30 prior to slitting is not required. Also, the hemostasis valve 25 may be slit while in place within the hub 15.

The shaft integrated into the hub provides a consistent slit medium such that the cardiac surgical device is not displaced from its position or location in or near the cardiac tissue. Such a slittable device reduces the time required for the procedure by reducing the chance of dislodging the surgical device during the removal of the delivery device from about the surgical device.

Although the present invention has been described with reference to preferred embodiments, persons skilled in the art will recognize that changes may be made in form and detail without departing from the spirit and scope of the invention.

What is claimed is:

1. A slittable delivery device for the delivery of a cardiac surgical device, the delivery device comprising:
    a slittable hub having a proximal end and a distal end;
    a slittable shaft integrated into the hub;
    wherein a proximal portion of the slittable shaft longitudinally splits into an exposed portion, wherein the exposed portion extends from the distal end of the slittable hub to the proximal end of the slittable hub to form a segment of a circumferential surface of the slittable hub, and wherein a slit is formed through the exposed portion upon removal of the slittable delivery device;
    a hemostasis valve contained substantially within the hub; and
    a cap on a proximal end of the hub and comprising an opening in the cap extending radially outward from a point near a radial center of the cap through a circumferential edge of the cap.

2. The delivery device of claim 1, wherein the cap at least partially encloses the valve within the hub.

3. The delivery device of claim 1, wherein the cap is coupled to the hub.

4. The delivery device of claim 1, wherein the delivery device is at least one of a catheter or sheath.

5. The delivery device of claim 1, wherein the cardiac surgical device is at least one of an implantable cardiac electrotherapy lead, an inner catheter, an inner sheath, a stylet, a guidewire and a sensor.

6. A slittable delivery device for the delivery of a cardiac surgical device, the delivery device comprising:
    a slittable shaft formed of at least a first material;
    a slittable hub coupled to the shaft and including a wall including a first wall segment and a second wall segment, wherein the first wall segment includes at least the first material and the second wall segment includes at least a second material that is at least one of harder and more rigid than the first material, and wherein the first and second wall segments extend from a distal end of the slittable hub to a proximal end of the slittable hub;
    a hemostasis valve contained substantially within the hub; and
    a cap on a proximal end of the hub and comprising an opening in the cap extending radially outward from a point near a radial center of the cap through a circumferential edge of the cap.

7. The delivery device of claim 6, wherein the second wall segment forms a substantially greater percentage of the wall surface than the first wall segment.

8. The delivery device of claim 6, wherein the device is at least one of a catheter or sheath.

9. The delivery device of claim 6, wherein the first and second wall segments are longitudinally extending wall segments.

10. The delivery device of claim 6, wherein the cardiac surgical device is at least one of an implantable cardiac electrotherapy lead, an inner catheter, an inner sheath, a stylet, a guidewire and a sensor.

11. The delivery device of claim 6, wherein the delivery device is at least one of a catheter or sheath.

12. A slittable delivery device for the delivery of a cardiac surgical device, the delivery device comprising:
    a slittable hub having a proximal end and a distal end;
    a slittable shaft integrated into the hub, a proximal end of the shaft longitudinally splitting into an exposed portion and an unexposed portion, the exposed portion extending from the proximal end of the slittable hub to the distal end of the slittable hub to form a segment of a circumferential surface of the slittable hub;
    a hemostasis valve contained substantially within the hub; and
    a cap on a proximal end of the hub and comprising an opening in the cap extending radially outward from a point near a radial center of the cap through a circumferential edge of the cap.

13. The delivery device of claim 12, wherein the cardiac surgical device is at least one of an implantable cardiac electrotherapy lead, an inner catheter, an inner sheath, a stylet, a guidewire and a sensor.

* * * * *